United States Patent [19]
Miller

[11] Patent Number: 5,865,836
[45] Date of Patent: Feb. 2, 1999

[54] NEEDLE-SUTURE COMBINATION

[75] Inventor: Eric C. Miller, Columbus, Ohio

[73] Assignee: United States Surgical Corporation, Norwalk, Conn.

[21] Appl. No.: 718,286

[22] Filed: Sep. 20, 1996

[51] Int. Cl.$^6$ .................................................. A61B 17/04
[52] U.S. Cl. ........................................ 606/228; 606/222
[58] Field of Search ..................................... 606/222–231

[56] References Cited

U.S. PATENT DOCUMENTS

| | | |
|---|---|---|
| 4,550,938 | 11/1985 | Nakanishi et al. . |
| 4,604,821 | 8/1986 | Moser . |
| 4,862,633 | 9/1989 | Hague et al. . |
| 5,051,107 | 9/1991 | Korthoff . |
| 5,063,704 | 11/1991 | Phillips . |
| 5,089,010 | 2/1992 | Korthoff . |
| 5,102,418 | 4/1992 | Granger et al. . |
| 5,123,911 | 6/1992 | Granger et al. . |
| 5,139,514 | 8/1992 | Korthoff et al. . |
| 5,226,912 | 7/1993 | Kaplan et al. . |
| 5,417,690 | 5/1995 | Sennett et al. . |
| 5,454,834 | 10/1995 | Boebel et al. ........................ 606/231 |
| 5,569,301 | 10/1996 | Granger et al. . |

OTHER PUBLICATIONS

Leo J. Klinger and George A. Kurisky, "MP35N Alloy—the Ultimate Wire Material," Maryland Specialty Wire Inc., Cockeysville, Md.

*Primary Examiner*—William Lewis

[57] ABSTRACT

A needle-suture combination includes a suture having first and second portions, the first portion having a pliability greater than that of the second portion. The needle is preferably a double tipped shuttle needle having a lateral aperture into which the suture is affixed. In one embodiment the first portion of the suture is multifilament suture material that is connected to a monofilament second portion by means of shrink wrap type tubing. In another embodiment the entire suture is an integral length of monofilament material, the first portion being a reduced diameter section of the monofilament suture.

10 Claims, 4 Drawing Sheets

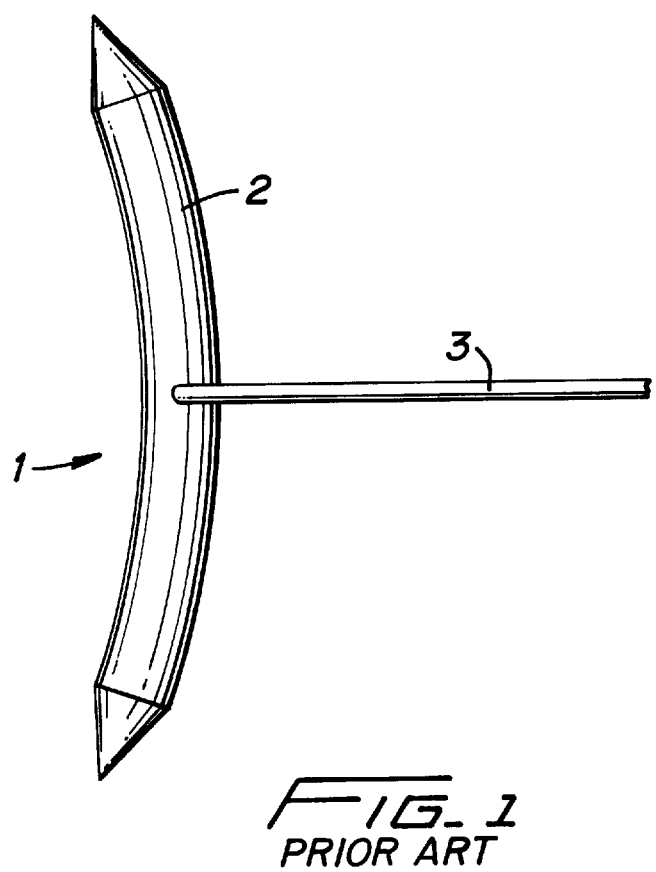
FIG_1
PRIOR ART
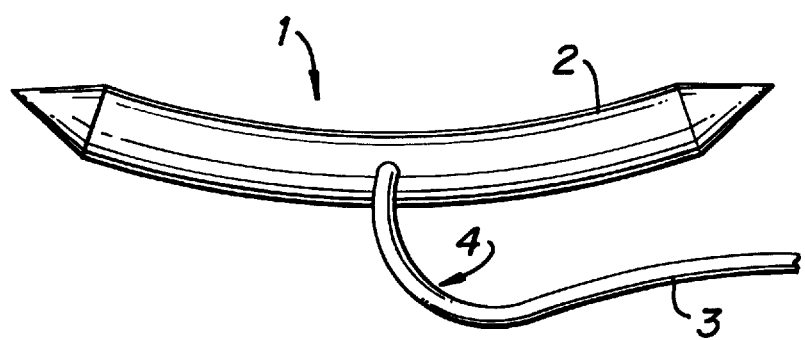
FIG_2
PRIOR ART

NEEDLE-SUTURE COMBINATION

BACKGROUND

1. Technical Field

The present specification is directed to a surgical suture, particularly, a suture used in combination with a double tipped needle.

2. Background of the Art

Surgical sutures are well known in the art. Surgical sutures can be monofilament or multifilament and can be fabricated from bioabsorbable or non-bioabsorbable material. Sutures are typically used in conjunction with surgical needles as part of needle-suture combinations.

Surgical needles are fabricated from metals such as stainless steel alloys which have the necessary requirements with respect to biocompatibility, strength, and the ability to take a sharp end and/or point when ground and polished. Many needles are single tipped. That is, the needle has a sharp pointed tip at one end and an axial bore or other structure at the other end which the suture is received and affixed by crimping, swaging, or other means. However, needles used in certain types of surgical stitching apparatus are double tipped. These needles, sometimes referred to as "shuttle" needles, are passed back and forth through body tissue between two jaws of the stitching apparatus. For such operations the needle has a sharp pointed tip at both ends to penetrate tissue going in two opposite directions. The suture is attached to the shuttle needle at a position spaced apart from the tips, usually at or in proximity to the midpoint of the needle.

It is preferable to use a monofilament suture in conjunction with the shuttle needle because monofilament sutures have a smoother surface and are characterized by less drag when passed through body tissue.

FIGS. 1 and 2 show a prior art needle-suture combination combining a double tipped shuttle needle 2 and a monofilament suture 3 attached to the middle of the shuttle needle 2. As can be seen in FIG. 2, when the shuttle needle 2 is moved a bend 4 occurs in the suture in the vicinity of the needle 3. Monofilament sutures are relatively stiff as compared to multifilament sutures. Therefore, the radius of the bend 4 is relatively large. This increased profile at the connection between the needle and suture can potentially lead to increased trauma to body tissue as the needle-suture combination is passed through tissue.

What is needed, therefore, is a shuttle needle-monofilament suture combination with a smaller suturing profile to reduce potential tissue trauma.

SUMMARY

A needle-suture combination is described herein which provides for a smaller suture bend radius and a smaller needle-suture profile as the needle-suture combination is passed through tissue. The needle suture combination includes a surgical needle, and a suture attached to the surgical needle, the suture having first and second portions, the first portion being characterized by a pliability which is greater than the pliability of the second portion.

This combination is advantageously used for shuttle needles having a pointed tip at each of two ends and a lateral suture receiving aperture into which the suture is attached, for example, by swaging.

In one embodiment the first portion of said suture is multifilament and the second portion is monofilament. The multifilament first portion has a first end inserted into the aperture of the needle and a second end attached to a first end of the monofilament second portion. The second end of the multifilament first portion of the suture and the first end of the monofilament second portion of the suture are connected, for example, by a shrinkable tube. Preferably, the shrinkable tubing has an outer diameter which is greater in the middle of the tubing than at the ends. The multifilament first portion has a length to diameter ratio of from about 5 to about 12.

In another embodiment, the first portion and second portion of the suture are integral portions of a monofilament suture, the first portion having a diameter of from about 20% to about 80% of the diameter of the second portion.

Generally, the needle can be fabricated from a material such as series 300 stainless steel alloy, series 400 stainless steel alloy, or nonferrous alloy, e.g., MP35N alloy. The suture can be fabricated from a non-bioabsorbable material such as silk, nylon, polyolefin, polyester, linen, or cotton, or bioabsorbable material such as polymers of glycolide, lactide, p-dioxanone, caprolactone, trimethylene, carbonate, and physical and chemical combinations thereof.

Also described herein is a method of making a surgical needle suture combination, the method including: providing a surgical needle having a pointed tip at each of two ends and a lateral suture receiving aperture; providing a length of multifilament suture material having first and second end portions, a length of monofilament suture material having a first end portion, and a length of shrinkable tubing; inserting the second end of the multifilament suture material and the first end portion of the monofilament suture material into the length of shrinkable tubing; causing the shrinkable tubing to shrink (for example, by heating) to a diameter small enough to grip and hold the suture ends inserted therein; and inserting the first end portion of the multifilament suture material into the aperture in the needle and affixing the first end portion therein.

A method is also provided for making the alternative embodiment of the needle suture combination, the alternative method comprising: providing a surgical needle having a pointed tip at each of two ends and a lateral suture receiving aperture; providing a length of monofilament suture material having a first end portion; inserting the first end portion of the monofilament suture material into the aperture in the needle and affixing the first end portion therein; and reducing the diameter of a predetermined portion of the monofilament suture material in the vicinity of the needle, for example, by convection or radiant heating to reversibly soften the predetermined portion of the monofilament suture material and by drawing the predetermined portion of the monofilament suture material by applying tension thereto.

BRIEF DESCRIPTION OF THE DRAWINGS

Various embodiments are described herein with reference to the drawings wherein:

FIGS. 1 and 2 are illustrations of a prior art needle suture combination;

DETAILED DESCRIPTION OF PREFERRED EMBODIMENT(S)

Figure 4:
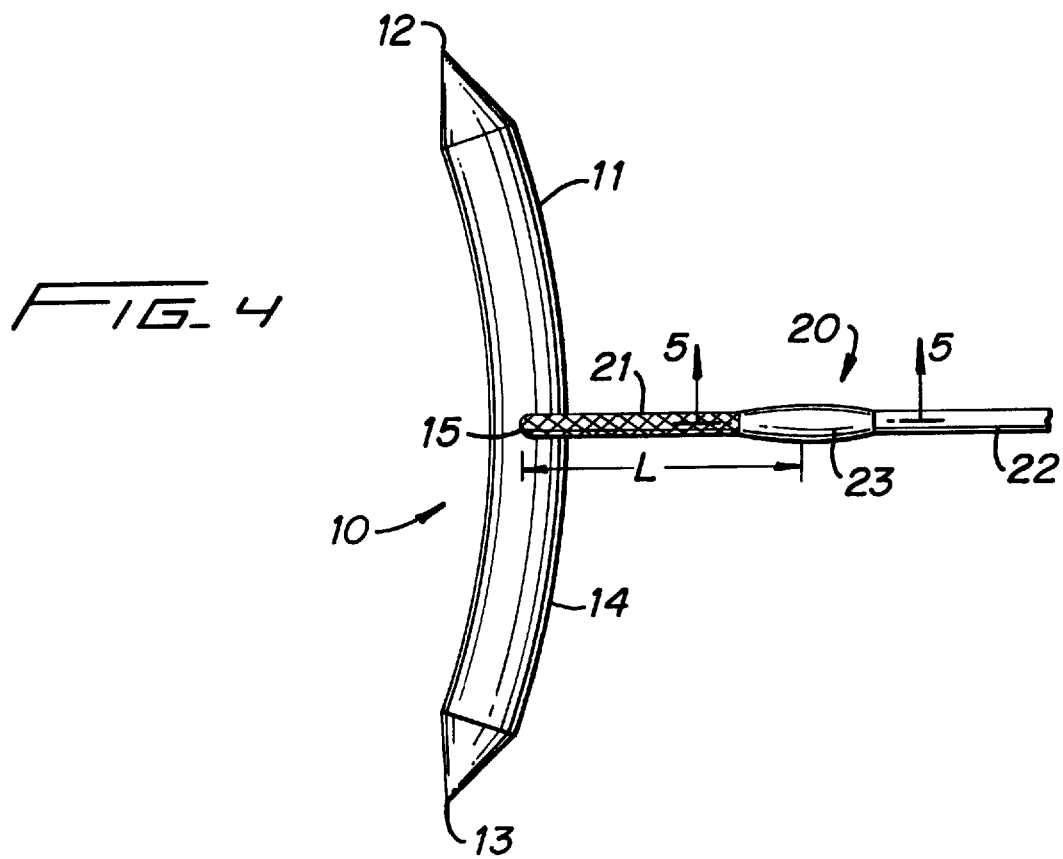
FIG. 4 is an elevational view of a first embodiment of the needle-suture combination described herein having a compound surgical suture.

Referring to FIG. 4 a needle-suture combination 10 is shown. The needle-suture combination 10 includes a shuttle needle 11 having a curved body portion 14 terminating at both ends in sharp pointed tips 12 and 13. An aperture 15 extends laterally through the needle 11 at about the midpoint of body portion 14.

The needle can be fabricated from any alloy suitable for use for the purpose described herein. Such alloys include, for example, series 300 stainless steel, series 400 stainless steel, and non-ferrous alloys such as MP35N alloy available from Maryland Specialty Wire Inc. of Cockeysville, Md. MP35N alloy has a nominal composition (by weight) of 35% nickel, 35% cobalt, 20% chromium, and 10% molybdenum.

Suture 20 includes a main monofilament portion 22 to which a multifilament leader 21 is attached by means of a shrink wrap type joiner 23.

Materials suitable for fabricating the suture described herein include non-bioabsorbable materials, such as, for example, silk, nylon, polyolefin, polyester, linen, and cotton. Also useful are bioabsorbable materials such as polymers of glycolide, lactide, p-dioxanone, caprolactone, and physical and chemical combinations thereof.

Use of a shrink wrap to attach sutures to needles is described for example in U.S. patent application Ser. Nos. 5,226,912, 5,139,514, and 5,123,911. Shrinkable plastic tubing for use in the compound suture 20 described herein is available from Raychem Corporation of Menlo Park, Calif. under the tradename Kynar™. This material is a polyvinylidene fluoride plastic which can be fabricated as shrinkable tubing. The tubing is typically extruded such that the inner diameter is less than the final desired inner diameter, i.e., the inner diameter of the shrinkable tubing after energy application in the attachment process used to combine the suture leader 21 with the suture main portion 22. Thereafter, the extruded shrinkable tubing is expanded radially outward through a radial expansion means to provide a tubing of expanded diameter. Such expanded tubing is thus adapted to shrink or "recover" to its original extruded inner diameter in response to the application of a predetermined amount of energy, e.g., heat. One type of polyvinylidene fluoride material useful for constructing the compound suture 20 is available from Raychem Corporation under the designation RT-850, and shrinks to about 50% of its radially expanded inner diameter when subjected to a temperature above about 175° C.

Figure 3A:
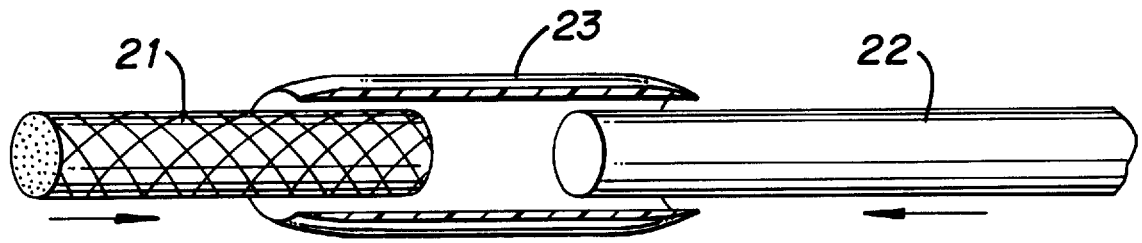
FIGS. 3A, 3B and 3C sequentially illustrate a method for joining suture lengths with shrinkable tubing.
Figure 3B:
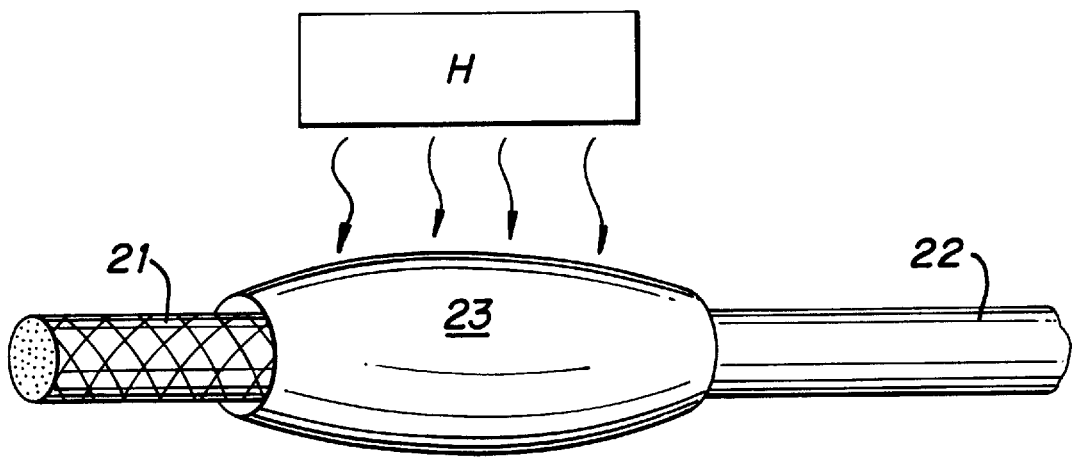
Figure 3C:
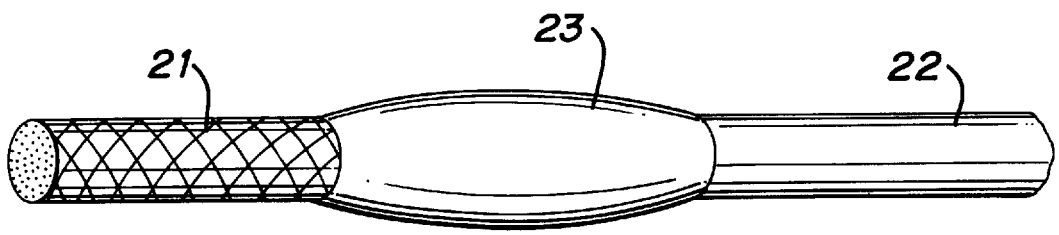

Referring to FIG. 3A, to form the joinder of the multifilament leader 21 and the monofilament main portion 22, the ends of the multifilament and monofilament strands are brought together in the axial bore of a shrink wrap tubing 23 in the uncontracted configuration. Referring to FIG. 3B, then heat is applied to the joint by heater H to contract the shrink wrap tubing 23, thereby gripping and holding the ends of leader 21 and monofilament main portion 22 in fixed attachment as shown in FIG. 3C. Heating can be accomplished by, for example, directing a stream of heated air at the shrink wrap tubing 23.

Figure 6:
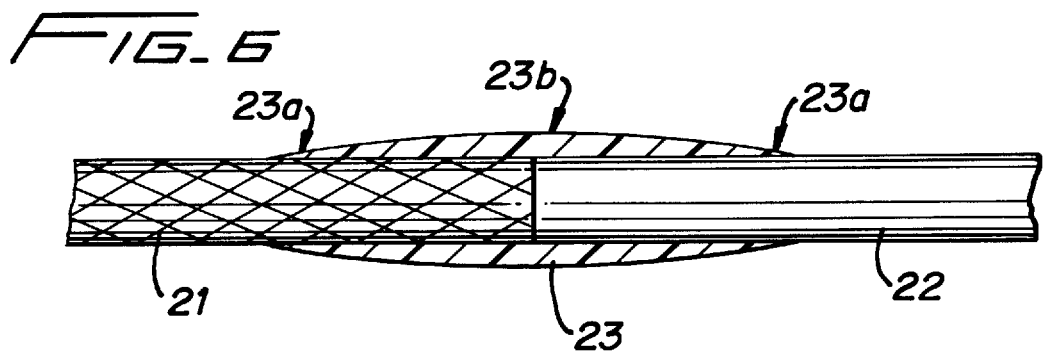
FIG. 6 is a partly sectional view of the joining of the first and second suture portions with shrinkable tubing.

Referring to FIG. 6, a detailed sectional view of the joint is shown. Preferably, the shrink wrap tubing 23 is tapered at both ends such that the outer diameter of shrink wrap tubing 23 at the ends 23a is less than the outer diameter at the middle 23b. The double ended taper facilitates the passing of the joint through the body tissue in both directions of suture travel.

Next the free end of the multifilament is inserted into aperture 15 of a needle 11. The suture leader 21 and needle 11 are preferably joined by crimping the needle 11 to fix the suture firmly within aperture 15 crimping operations for suture attachment are well known in the art.

Figure 5:
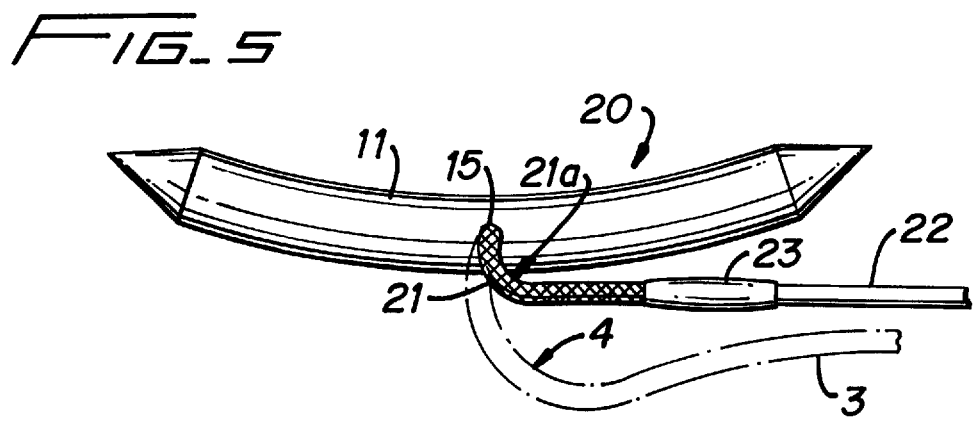
FIG. 5 is an elevational view of the first embodiment of the needle-suture combination illustrating the bend in the suture.

Referring now also to FIG. 5, the resulting needle-suture combination 10 includes a compound suture 20 having a multifilament leader portion 21 in the vicinity of the needle 11, the leader portion 21 having a significantly greater pliability than the rest of the suture. This feature enables the suture 20 to have a smaller, or tighter turning radius 21a than for a simple monofilament suture of the same diameter. See, for example, the relatively larger diameter. of bend 4 in a monofilament suture 3 which would result if the monofilament suture 3 were attached directly to aperture 15. This, feature in turn, results in a smaller needle-suture profile presented to the body tissue as the needle and suture are passed therethrough.

By way of illustration, a typical shuttle needle 11 of about 9 mm in length from tip to tip can be attached to a USP size 0 surgical suture (about 0.35–0.39 mm. diameter). The length L (FIG. 4) of the multifilament leader 21 extending from aperture 15 can be from about 2 to 4 mm. The ratio of leader length L to leader diameter can be from about 5 to about 12. Optimally the multifilament leader 21 has the same diameter as the monofilament main portion 22.

Figure 7:
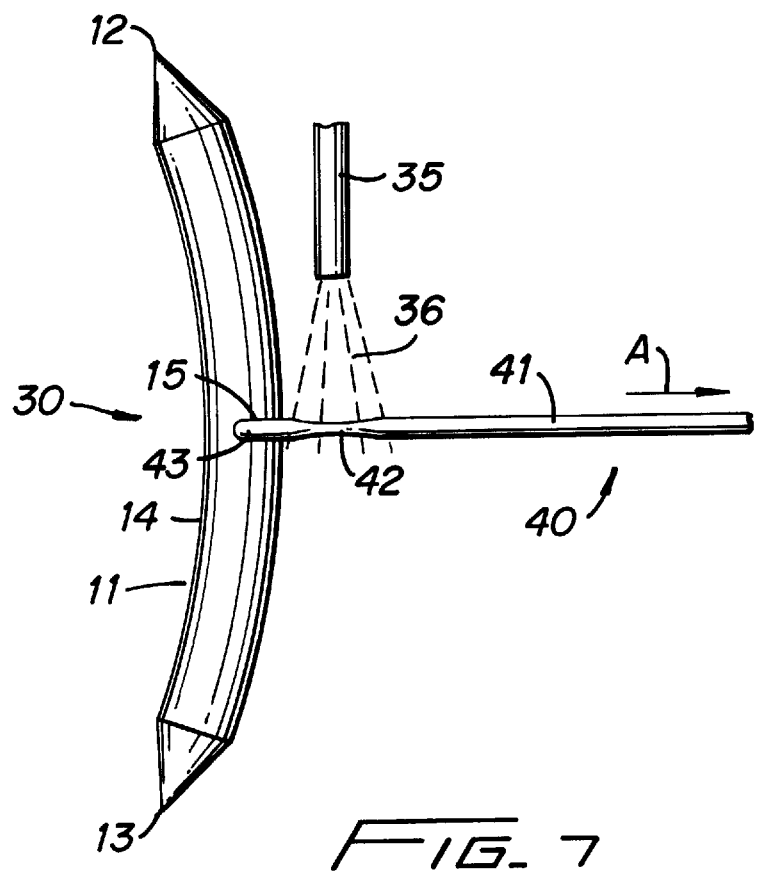
FIG. 7 illustrates a second embodiment of needle-suture combination showing formation of a reduced diameter portion.

Referring to FIG. 7 an alternative embodiment 30 of the invention is shown. Needle-suture combination 30 includes a shuttle needle 11 as described above having an arcuate body portion 14 terminating in sharp pointed tips 12 and 13. An aperture 15 extends laterally through needle 11 at or near the midpoint of the body portion 14.

Suture 40 is entirely monofilament. It is fabricated from a thermoplastic polymer and includes a main portion 41, and end portion 43 which is attached to the needle 11 by insertion in aperture 15. Increased pliability portion 42 comprises a narrow (i.e., narrow relative to the main portion 41) region in which the diameter has been reduced.

Reduction of suture diameter can be accomplished by heating portion 42 sufficient to reversibly soften the monofilament material while applying tension as shown by arrow A in order to draw the suture 40. The heater 35 can be any heating means suitable for the purposes herein such as convection or radiant heating. For example, heater 35 can be a hot air blower for projecting a stream 36 of air at a suitable softening temperature. Alternatively, heater 35 can be a radiant heater or laser. Portion 42 should be heated to the softening point of the polymer from which monofilament suture 40 is constructed. Typical softening points for various materials are set forth below in Table I.

The duration of heating time necessary to achieve softening of the monofilament material depends, inter alia, upon the diameter of the monofilament and manner of heating. While the suture portion 42 is in the softened condition, tension is applied in the direction of arrow A to draw the suture, thereby reducing the diameter of suture portion 42 and making it more pliable. After heating and drawing the suture portion 42 is permitted to cool to ambient temperature whereupon it returns to its initial condition.

The diameter of increased pliability section 42 after diameter reduction is preferably from about 20% to about 80% of the diameter of the main portion 41.

Figure 8:
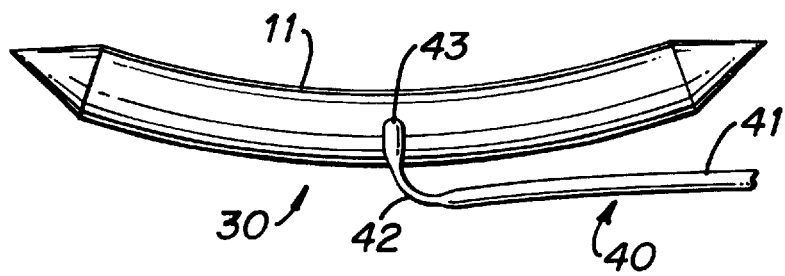
FIG. 8 illustrates the second embodiment of the needle-suture combination showing bending of the suture.

FIG. 8 shows the needle suture combination 30 in operating configuration wherein suture 40 is bent at the increased pliability portion 42.

It will be understood that various modifications may be made to the embodiments described herein. Therefore, the description should not be construed as limiting, but merely as exemplifications of preferred embodiments. Those skilled in the art will envision other modifications within the scope and spirit of the claims appended hereto.

What is claimed is:

1. A needle-suture combination, which comprises:
   a) a surgical needle having a pointed tip at each of two ends and a lateral suture receiving aperture disposed between the two ends; and
   b) a suture attached to the surgical needle, said suture having a first multifilament suture portion and second monofilament suture portion, said first suture portion being characterized by a pliability which is greater than the pliability of the second suture portion.

2. The needle-suture combination of claim 1, wherein the multifilament first portion has a first end inserted into the aperture of the needle and a second end connected to a first end of the monofilament second portion.

3. The needle-suture combination of claim 2, wherein the second end of the multifilament first portion of the suture and the first end of the monofilament second portion of the suture are connected by a shrinkable tubing.

4. The needle-suture combination of claim 3, wherein the shrinkable tubing has an outer diameter which is greater in the middle of the tubing than at the ends.

5. The needle-suture combination of claim 1, wherein the multifilament first portion has a length to diameter ratio of from about 5 to about 12.

6. The needle-suture combination of claim 1, wherein the needle is fabricated from a material selected from the group consisting of series 300 stainless steel alloy, series 400 stainless steel alloy, and non-ferrous alloy.

7. The needle-suture combination of claim 1, wherein the suture is fabricated from a non-bioabsorbable material selected from the group consisting of silk, nylon, polyolefin, polyester, linen and cotton.

8. The needle-suture combination of claim 1, wherein the suture is fabricated from a bioabsorbable material selected from the group consisting of polymers of glycolide, lactide, p-dioxanone, caprolactone, trimethylene carbonate, and physical and chemical combinations thereof.

9. A needle-suture combination, which comprises:
   a) a surgical needle having a pointed tip at each of two ends and a lateral suture receiving aperture disposed between the two ends; and
   b) an integral monofilament suture attached to said surgical needle, said suture having first and second portions, said first suture portion having a diameter from about 20% to about 8% of the diameter of the second suture portion and being characterized by a pliability which is greater than the pliability of the second suture portion.

10. A needle-suture combination, which comprises:
    a) a surgical needle; and
    b) a suture attached to said surgical needle, said suture having first and second portions, said first suture portion being disposed between the surgical needle and the second suture portion and being characterized by a pliability which is greater than the pliability of the second suture portion, wherein the first suture portion is a multifilament suture portion and the second suture portion is a monofilament suture portion.

* * * * *